(12) United States Patent
Indukuri et al.

(10) Patent No.: US 9,181,256 B2
(45) Date of Patent: Nov. 10, 2015

(54) SALTS OF SITAGLIPTIN, PROCESS FOR THE PREPARATION AND PHARMACEUTICAL COMPOSITION THEREFORE

(71) Applicant: Laurus Labs Private Limited, Hyderabad (IN)

(72) Inventors: Venkata Sunil Kumar Indukuri, Hyderabad (IN); Seeta Ramanjaneyulu Gorantla, Hyderabad (IN); Vamsee Krishna Muppidi, Hyderabad (IN); Satyanarayana Chava, Hyderabad (IN)

(73) Assignee: Laurus Labs Private Ltd., Hyderabad (IN)

( * ) Notice: Subject to any disclaimer, the term of this patent is extended or adjusted under 35 U.S.C. 154(b) by 5 days.

(21) Appl. No.: 13/985,490

(22) PCT Filed: Oct. 12, 2012

(86) PCT No.: PCT/IN2012/000680
§ 371 (c)(1),
(2) Date: Nov. 22, 2013

(87) PCT Pub. No.: WO2013/054364
PCT Pub. Date: Apr. 18, 2013

(65) Prior Publication Data
US 2014/0073791 A1   Mar. 13, 2014

(30) Foreign Application Priority Data

Oct. 14, 2011   (IN) .......................... 3528/CHE/2011

(51) Int. Cl.
*C07D 487/04* (2006.01)
*A61K 31/4985* (2006.01)
*C07C 57/42* (2006.01)

(52) U.S. Cl.
CPC .......... *C07D 487/04* (2013.01); *A61K 31/4985* (2013.01); *C07C 57/42* (2013.01)

(58) Field of Classification Search
CPC .................................................. C07D 487/04
See application file for complete search history.

(56) References Cited

U.S. PATENT DOCUMENTS

| 6,699,871 B2 | 3/2004 | Edmondson et al. |
| 7,326,708 B2 | 2/2008 | Cypes et al. |

FOREIGN PATENT DOCUMENTS

| CN | 101863891 A | 10/2010 |
| WO | WO-2005020920 A2 | 3/2005 |
| WO | WO-2005030127 A2 | 4/2005 |
| WO | WO-2005072530 A1 | 8/2005 |
| WO | WO-2006033848 A1 | 3/2006 |
| WO | WO-2007-035198 A2 | 3/2007 |
| WO | WO-2009085990 A2 | 7/2009 |
| WO | WO-2010000469 A2 | 1/2010 |
| WO | WO-2010012781 A2 | 2/2010 |
| WO | WO-2010/092090 A2 | 8/2010 |
| WO | WO 2010092090 A2 * | 8/2010 |
| WO | WO-2010117738 A2 | 10/2010 |
| WO | WO-2011018494 A1 | 2/2011 |
| WO | WO-2012076973 A2 | 6/2012 |

OTHER PUBLICATIONS

Moonsan, P., et al. "Insulin-Releasing Properties of a Series of Cinnamic Acid Derivatives In Vitro and In Vivo." J. Agric. Food Chem. (2008), vol. 56, pp. 7838-7844.*
Jung, U., et al. "Antihyperglycemic and Antioxidant Properties of Caffeic Acid in db/db Mice." J. Pharmacology & Experimental Therapeutics. (2006), vol. 318, No. 2, pp. 476-483.*
Rai, V., et al. "Chromatographic Estimation of p-Coumaric Acid and Triacontanol in an Ayurvedic Root Drug Patala (Stereospermum suaveolens Roxb.)." J. Chromatographic Science. (2009), vol. 47, pp. 936-939.*
Menon, et al. "Ferulic Acid: Therapeutic Potential Through Its Antioxidant Property." J. Clin. Biochem. Nutr. (2007), vol. 40, pp. 92-100.*
Wikipedia. "Alkane." (c) Apr. 24, 2009. Available from: <http://web.archive.org/web/20090424073225/http://en.wikipedia.org/wiki/Alkane>.*
International Search Report, Jul. 4, 2013.

* cited by examiner

*Primary Examiner* — Noble Jarrell
*Assistant Examiner* — John S Kenyon
(74) *Attorney, Agent, or Firm* — Blank Rome LLP (57) ABSTRACT

The present invention relates to pharmaceutically acceptable acid addition salts of sitagliptin, in particular anti-oxidant acid addition salts of sitagliptin and a process for its preparation. The present invention also provides a pharmaceutical composition using the pharmaceutically acceptable acid addition salts of sitagliptin.

2 Claims, 10 Drawing Sheets

LAURUS LABS PVT LTD

LAURUS LABS PVT LTD

LAURUS LABS PVT LTD

LAURUS LABS PVT LTD

LAURUS LABS PVT LTD

LAURUS LABS PVT LTD

LAURUS LABS PVT LTD

LAURUS LABS PVT LTD

LAURUS LABS PVT LTD

SALTS OF SITAGLIPTIN, PROCESS FOR THE PREPARATION AND PHARMACEUTICAL COMPOSITION THEREFORE

CROSS-REFERENCE TO RELATED APPLICATIONS

The present application claims the benefit of International Patent Application No. PCT/IN2012/000680, filed Oct. 12, 2012, which in turn claims priority to Indian Patent Application No. 3528/CHE/2011, filed Oct. 14, 2011, the entire disclosures which are incorporated herein by reference.

PRIORITY

This application claims the benefit under Indian Provisional Application No. 3528/CHE/2011, filed Oct. 14, 2011, the content of each of which is incorporated by reference herein.

FIELD OF THE INVENTION

The present invention generally relates to pharmaceutically acceptable acid addition salts of sitagliptin, in particular anti-oxidant acid addition salts of sitagliptin, processes for its preparation and a pharmaceutical composition containing the same.

BACKGROUND OF THE INVENTION

Sitagliptin, (3R)-3-amino-1-[9-(trifluoromethyl)-1,4,7,8-tetrazabicyclo[4.3.0]nona-6,8-dien-4-yl]-4-(2,4,5-trifluorophenyl)butan-↑-one, has the following chemical structure:

Sitagliptin

Sitagliptin is an orally-active dipeptidyl peptidase-4 (DPP-IV) enzyme inhibitor that improves glycemic control in patients with Type 2 diabetes mellitus by slowing the inactivation of incretin hormones. Sitagliptin may be used as a monotherapy, as an adjunct to diet and exercise, or in combination with metformin or a PPARγ agonist (e.g., thiazolidinediones). Sitagliptin is currently marketed in its phosphate salt in the United States under the tradename JANUVIA™ in its monohydrate form JANUVIA™ is indicated to improve glycemic control in patients with type 2 diabetes mellitus.

U.S. Pat. No. 6,699,871 ("the '871 patent") discloses a class of beta-amino-tetrahydrotriazolo[4,3-a]pyrazines such as Sitagliptin and its hydrochloride salt form, a potent inhibitor of DPP-IV enzyme. Other pharmaceutically acceptable salts of this compound are generically encompassed within the scope of the '871 patent. It also discloses a process for the preparation of sitagliptin and related compounds.

U.S. Pat. No. 7,326,708 discloses dihydrogen phosphate salt of sitagliptin and crystalline hydrate thereof, in particular a crystalline monohydrate and processes for the preparation thereof. Crystalline polymorphs of sitagliptin dihydrogen phosphate anhydrate such as Form I, Form II, Form III and Form IV are disclosed in Patent publication No. WO 2005/020920 and WO 2005/030127. Amorphous sitagliptin dihydrogen phosphate is disclosed in Patent publication No. WO 2006/033848.

Patent publication No. WO 2005/072530 discloses crystalline acid addition salts of sitagliptin and hydrates thereof, wherein the acid addition salt is selected from the group consisting of hydrochloric acid, tartaric acid, benzene sulfonic acid, p-toluene sulfonic acid and 10-caphor sulfonic acid.

Patent publication No. WO 2007/035198 discloses crystalline anhydrate form of dodecyl sulfate salt of sitagliptin and process for the preparation thereof.

Patent publication No. WO 2009/085990 discloses crystalline forms of salts of sitagliptin such as sulfuric acid, hydrobromic acid, methane sulfonic acid, acetic acid, benzoic acid, oxalic acid, succinic acid, mandelic acid, fumaric acid, di-p-tolyl-L-tartaric acid and lactic acid and process for the preparation thereof.

Patent publication No. WO 2010/000469 discloses crystalline forms of sitagliptin monobasic, dibasic and tribasic acid addition salts such as hydrochloric acid (Form I and Form II), sulfuric acid (Form I and Form II), methane sulfonic acid (Form I and Form II), fumaric acid (Form I and Form II), malonic acid, malic acid, succinic acid (Form I, Form II and Form III), lactic acid, glycolic acid, maleic acid (Form I and Form II), citric acid (crystalline and amorphous Form), aspartic acid and mandelic acid and process for the preparation thereof.

Patent publication No. WO 2010/012781 ("the '781 publication") discloses salts of sitagliptin such as ethanedisulfonic acid, galactaric acid, thiocyanic acid, and glutaric acid. The '781 publication further discloses crystalline forms of sitagliptin acid addition salts such as galactaric acid (Form I), L-malic acid (Form I) D-gluconic acid (Form I), succinic acid (Form I), hydrobromic acid (Form I), thiocyanic acid (Form I), oxalic acid (Form I), L-aspartic acid (Form I), ethanedisulfonic acid (Form I), pyroglutamic acid (Form I), glutaric acid (Form I), and acetic acid (Form I).

Patent publication No. WO 2010/092090 discloses acid addition salts of sitagliptin, wherein the acid addition salt is selected from the group consisting of D-glucuronic acid, L-glucuronic acid, glutaric acid, sulfuric acid, L-Lactic acid, D-Lactic acid, ethane sulfonic acid, oxalic acid, acetic acid, L-mandelic acid, D-mandelic acid, capric acid, benzoic acid, hippuric acid, trans-cinnamic acid, malonic acid, citric acid, 1-hydroxy-2-naphtolic acid, crotonic acid and ascorbic acid and process for the preparation thereof.

Patent publication No. WO 2010/117738 discloses crystalline forms of sitagliptin acid addition salts such as sitagliptin sulfate (Form S1, Form S2, Form S3, Form S5, Form S6, Form S7 and Form S8), sitagliptin acetate (Form E1), sitagliptin dibenzoyl-D-tartrate (Form D1 and D2), sitagliptin fumarate (Form F1 and F2), sitagliptin malate (Form M1 and Form M2), sitagliptin oxalate (Form O1 and Form O2), sitagliptin Quinate (Form Q1), sitagliptin succinate (Form U1), sitagliptin mandelate (Form N1, Form N2, Form N3, Form N4 and amorphous form), sitagliptin lactate (Form L1, Form L2, Form L3 and Form L4), sitagliptin maleate (Form A1), sitagliptin S-mandelate (Form N3), sitagliptin L-malate (Form I1), sitagliptin R-(−)-mandelate (Form N5 and Form N6), sitagliptin Orotate (amorphous form).

Patent Publication No. CN101863891 ("the '891 publication") discloses inorganic salts of sitagliptin such as sodium bisulfate, potassium bisulfate, cesium bisulfate and ammonium bisulfate salt of sitagliptin; sodium dihydrogen phosphate, potassium dihydrogen phosphate, cesium dihydrogen phosphate and ammonium dihydrogen phosphate salt of sitagliptin. The '891 publication further discloses a complex salts of sitagliptin such as sitagliptin sulfate or phosphate salt complex with aminobutanetriol, aminopropanediol, amino ethanol, glucosamine, arginine, ornithine, citrulline or lysine.

Patent publication No. WO 2011/018494 discloses fumarate salt of sitagliptin, wherein the ratio of sitagliptin to fumaric acid is 1:0.6 to 1:1.3 and process for the preparation thereof.

Different salt forms of the same pharmaceutically active moiety differ in their physical properties such as melting point, solubility, etc. These properties may appreciably influence pharmaceutical properties such as dissolution rate and bioavailability. In addition, polymorphism, the occurrence of different crystal forms, is a property of some molecules and molecular complexes. A single molecule may give rise to a variety of polymorphs having distinct crystal structures and physical properties like melting point, thermal behaviours (e.g. measured by thermogravimetric analysis ("TGA"), or differential scanning calorimetry ("DSC"), X-ray diffraction pattern (XRPD), infrared absorption fingerprint, and solid state NMR spectrum. One or more of these techniques may be used to distinguish different polymorphic forms of a compound.

Discovering new polymorphic forms and solvates of a pharmaceutical product can provide materials having desirable processing properties, such as ease of handling, ease of processing, storage stability, and ease of purification or as desirable intermediate crystal forms that facilitate conversion to other polymorphic forms. New polymorphic forms and solvates of a pharmaceutically useful compound or salts thereof can also provide an opportunity to improve the performance characteristics of a pharmaceutical product. It enlarges the repertoire of materials that a formulation scientist has available for formulation optimization, for example by providing a product with different properties, e.g., better processing or handling characteristics, improved dissolution profile, or improved shelf-life.

In view of the foregoing, it would be desirable to provide new salt forms of sitagliptin. Further, it would be desirable to have reliable processes for producing these salt forms of sitagliptin. Additionally, the various salt forms of sitagliptin could be used to prepare improved pharmaceutical compositions.

SUMMARY OF THE INVENTION

It has now been found that new acid addition salt forms of sitagliptin; in particular anti-oxidant acid addition salts of sitagliptin can be obtained which have improved properties as compared to presently-known form of such compound. In an aspect, the improved property is selected from the group consisting of: increased solubility, increased dissolution, increased bioavailability, increased dose response, decreased hygroscopicity, decreased from diversity, more desired morphology, or other property described herein.

Accordingly, in one embodiment, the present invention provides pharmaceutically acceptable acid addition salts of sitagliptin, in particular anti-oxidant acid addition salts of sitagliptin, or hydrates or solvates thereof.

In accordance with a second embodiment, the present invention provides an acid addition salts of sitagliptin, wherein the acid is an anti-oxidant acid and is selected from the group consisting of cinnamic acid and its derivatives such as p-coumaric acid, Ferulic acid, Sinapic acid, Caffeic acid, Chlorogenic acid and the like; benzoic acid and its derivatives such as p-hydroxy benzoic acid, Vanillic acid, Syringic acid, Protocatechuic acid, 4-(4-phenoxybenzoyl)benzoic acid and the like; and Quinic acid.

In accordance with a third embodiment, the present invention further provides acid addition salts, particularly anti-oxidant acid addition salts of sitagliptin exist in the form of polymorphs of salts, co-crystals, or polymorphs of co-crystals.

In accordance with a fourth embodiment, the present invention provides a process for preparing acid addition salts of sitagliptin comprising a) providing a mixture comprising sitagliptin base and an anti-oxidant acid and b) isolating the acid addition salts of sitagliptin; wherein the anti-oxidant acid is selected from the group consisting of cinnamic acid and its derivatives such as p-coumaric acid, Ferulic acid, Sinapic acid, Caffeic acid, Chlorogenic acid and the like; benzoic acid and its derivatives such as p-hydroxy benzoic acid, Vanillic acid, Syringic acid, Protocatechuic acid, 4-(4-phenoxybenzoyl)benzoic acid and the like; and Quinic acid.

In accordance with a fifth embodiment, the present invention provides a pharmaceutical composition comprising acid addition salt forms of sitagliptin prepared by the processes of the present invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

The present invention addresses a need in the art by providing new acid addition salt forms of sitagliptin, or hydrates or solvates thereof; in particular anti-oxidant acid addition salts of sitagliptin or hydrates or solvates thereof and processes for their preparation.

The present inventors have identified new acid addition salt forms of sitagliptin, particularly anti-oxidant acid addition salts. These salt forms may be in the form of solvates, hydrates, polymorphs of salts, co-crystals, or polymorphs of co-crystals.

It has surprisingly been found that when sitagliptin and a selected anti-oxidant acid component are allowed to form a salt form, the resulting salt form may give rise to improved properties of the sitagliptin, as compared to the sitagliptin in a free form (including free base, hydrates, solvates etc.), particularly with respect to: solubility, dissolution, bioavailability, stability, Cmax, Tmax, processability, longer lasting therapeutic plasma concentration, hygroscopicity, decrease in form diversity (including polymorphism and crystal habit), change in morphology or crystal habit, etc. For example, a salt form of sitagliptin is particularly advantageous where the original sitagliptin is insoluble or sparingly soluble in water. The salt form properties conferred upon the sitagliptin are also useful because the bioavailability of the sitagliptin can be improved and the plasma concentration and/or serum concentration of the sitagliptin can be improved.

The anti-oxidant acids used in the present invention are not only intended for formation of pharmaceutically acceptable salt form of sitagliptin, itself can advantageously be useful for therapeutical use, for example, anti-oxidant acids can stabilize the body's metabolism by defending against damage caused by free radicals. The anti-oxidant acid salts of sitagliptin are more effective with respect to therapeutic activity of the sitagliptin as compared to the sitagliptin salt form with non anti-oxidant acids described in the afore mentioned literature.

Accordingly, in one embodiment, the present invention provides pharmaceutically acceptable acid addition salts of sitagliptin or hydrates or solvates thereof, in particular anti-oxidant acid addition salts of sitagliptin or hydrates or solvates thereof.

The ratio of sitagliptin to anti-oxidant acid compound may be stoichiometric or non-stoichiometric according to the present invention. For example, 1:1, 1.5:1, 1:1.5, 2:1 and 1:2 ratios of sitagliptin: anti-oxidant acid are acceptable.

In another embodiment, the anti-oxidant acid compound selected from at least one of anti-oxidant acid compounds known in the art. For example, the anti-oxidant acid includes, but are not limited to cinnamic acid and its derivatives such as p-coumaric acid, Ferulic acid, Sinapic acid, Caffeic acid, Chlorogenic acid and the like; benzoic acid and its derivatives such as p-hydroxy benzoic acid, Vanillic acid, Syringic acid, Protocatechuic acid, 4-(4-phenoxybenzoyl)benzoic acid and the like; and Quinic acid.

In one embodiment, the present invention provides sitagliptin caffate or hydrate or solvate thereof.

In another embodiment, the present invention provides sitagliptin caffate in crystalline form.

In another embodiment, the present invention provides crystalline sitagliptin caffate ethanolate.

Figure 1:
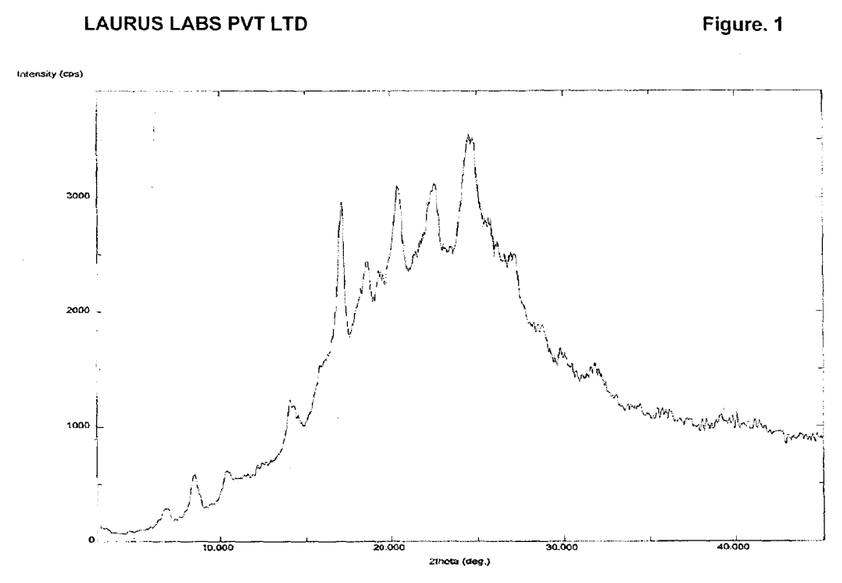
FIG. 1 is the characteristic powder X-ray diffraction (XRD) pattern of Sitagliptin caffate Form I.

In another embodiment, the present invention provides crystalline sitagliptin caffate ethanolate (Form I), characterized by an X-Ray diffraction (XRD) pattern substantially in accordance with FIG. 1.

In another embodiment, the present invention provides crystalline sitagliptin caffate isopropyl ether solvate.

Figure 2:
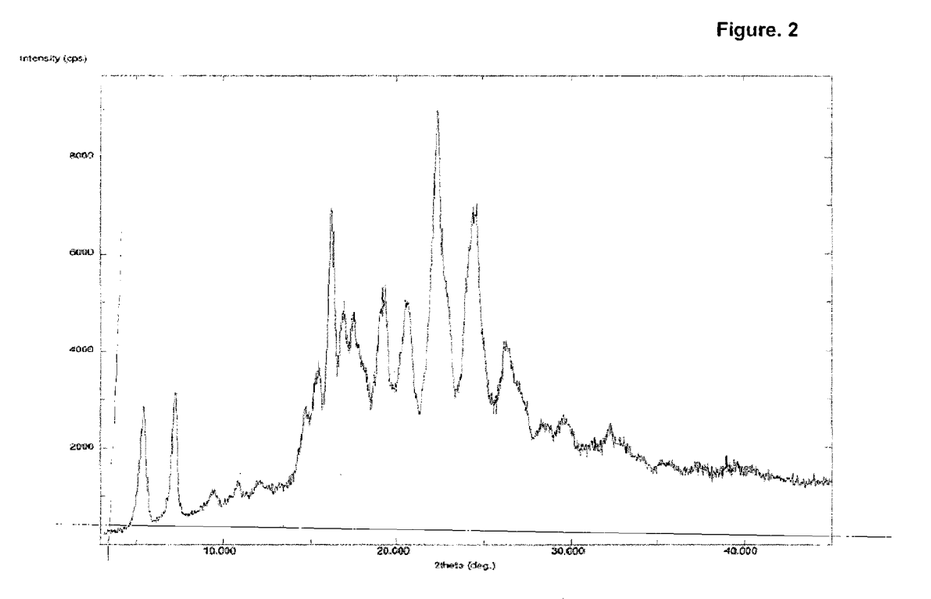
FIG. 2 is the characteristic powder X-ray diffraction (XRD) pattern of Sitagliptin caffate Form II.

In another embodiment, the present invention provides crystalline sitagliptin caffate isopropyl ether solvate (Form II), characterized by an X-Ray diffraction (XRD) pattern substantially in accordance with FIG. 2.

In another embodiment, the present invention provides crystalline sitagliptin caffate acetone solvate.

Figure 3:
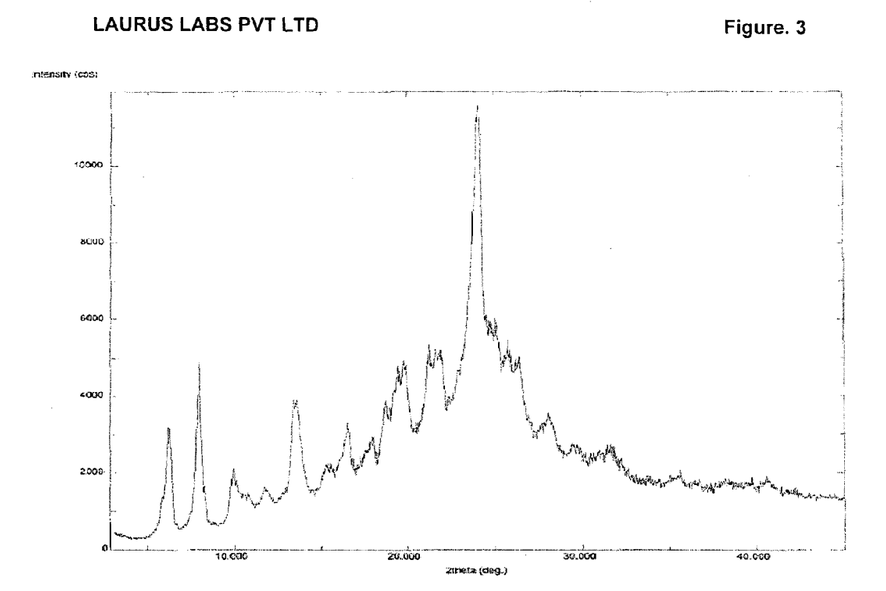
FIG. 3 is the characteristic powder X-ray diffraction (XRD) pattern of Sitagliptin caffate Form III.

In another embodiment, the present invention provides crystalline sitagliptin caffate acetone solvate (Form III), characterized by an X-Ray diffraction (XRD) pattern substantially in accordance with FIG. 3.

In another embodiment, the present invention provides crystalline sitagliptin caffate tetrahydrofuran (THF) solvate.

Figure 4:
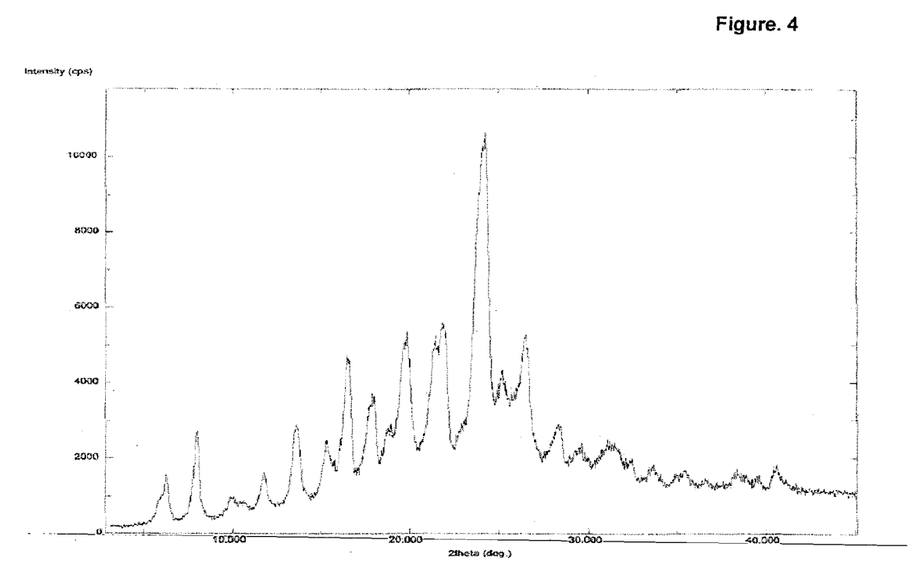
FIG. 4 is the characteristic powder X-ray diffraction (XRD) pattern of Sitagliptin caffate Form IV.

In another embodiment, the present invention provides crystalline sitagliptin caffate THF solvate (Form IV), characterized by an X-Ray diffraction (XRD) pattern substantially in accordance with FIG. 4.

In another embodiment, the present invention provides crystalline sitagliptin caffate Acetonitrile solvate.

Figure 5:
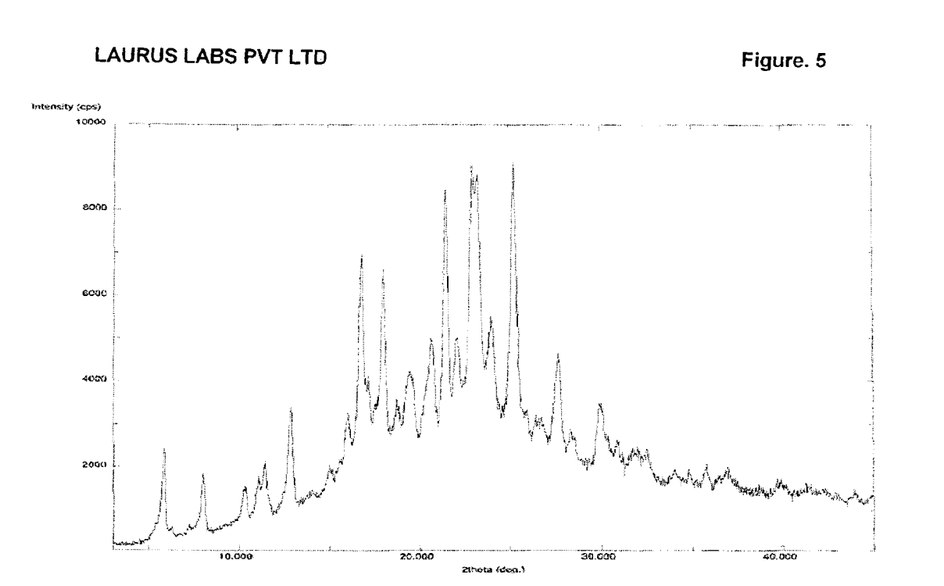
FIG. 5 is the characteristic powder X-ray diffraction (XRD) pattern of Sitagliptin caffate Form V

In another embodiment, the present invention provides crystalline sitagliptin caffate Acetonitrile solvate (Form V), characterized by an X-Ray diffraction (XRD) pattern substantially in accordance with FIG. 5.

In another embodiment, the present invention provides crystalline sitagliptin caffate Ethyl acetate solvate.

Figure 6:
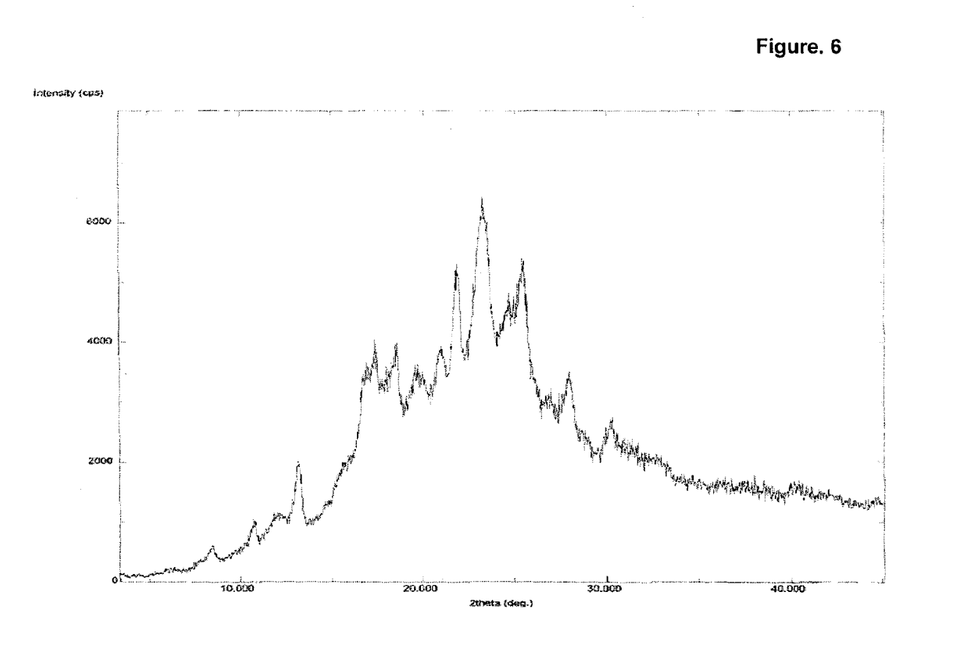
FIG. 6 is the characteristic powder X-ray diffraction (XRD) pattern of Sitagliptin caffate Form VI

In another embodiment, the present invention provides crystalline sitagliptin caffate Ethyl acetate solvate (Form VI), characterized by an X-Ray diffraction (XRD) pattern substantially in accordance with FIG. 6.

In another embodiment, the present invention provides sitagliptin caffate in an amorphous form.

Figure 7:
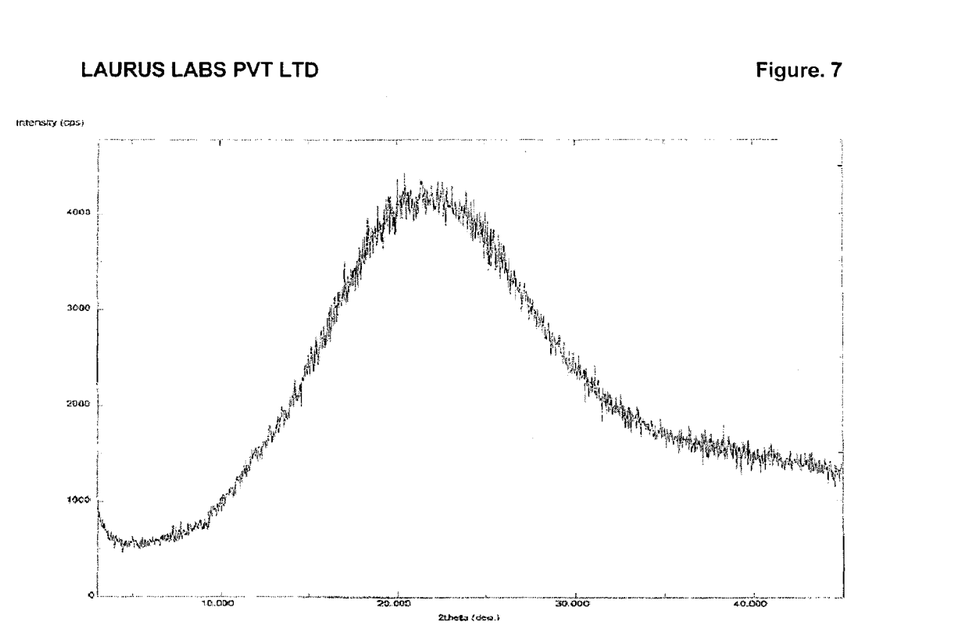
FIG. 7 is the characteristic powder X-ray diffraction (XRD) pattern of Sitagliptin caffate amorphous Form.

In yet another embodiment, the present invention provides sitagliptin caffate in an amorphous form, characterized by an X-Ray diffraction (XRD) pattern substantially in accordance with FIG. 7.

In another embodiment, the present invention provides sitagliptin ferulate or hydrate or solvate thereof.

In another embodiment, the present invention provides sitagliptin ferulate in crystalline form.

In another embodiment, the present invention provides crystalline sitagliptin ferulate Acetonitrile solvate.

Figure 8:
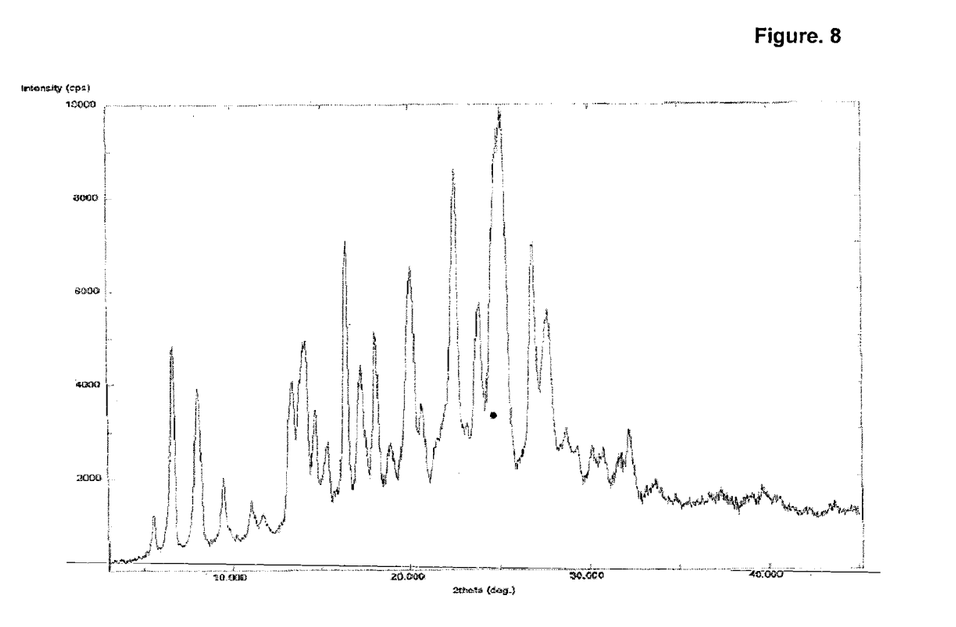
FIG. 8 is the characteristic powder X-ray diffraction (XRD) pattern of Sitagliptin ferulate Form I.

In another embodiment, the present invention provides crystalline sitagliptin ferulate Acetonitrile solvate (Form I), characterized by an X-Ray diffraction (XRD) pattern substantially in accordance with FIG. 8.

Figure 9:
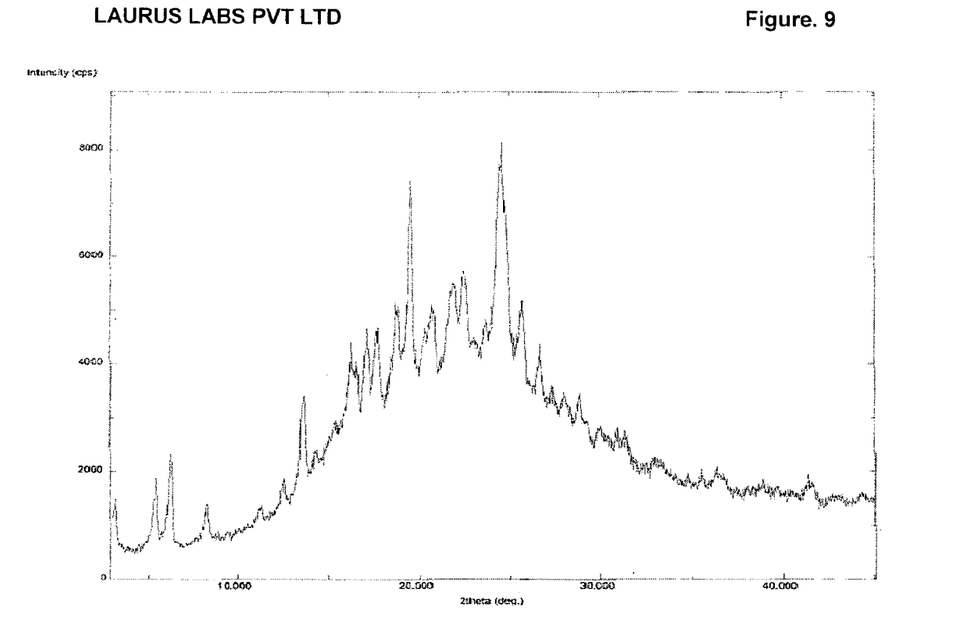
FIG. 9 is the characteristic powder X-ray diffraction (XRD) pattern of Sitagliptin ferulate Form II.

In another embodiment, the present invention provides crystalline sitagliptin ferulate (Form II), characterized by an X-Ray diffraction (XRD) pattern substantially in accordance with FIG. 9.

Figure 10:
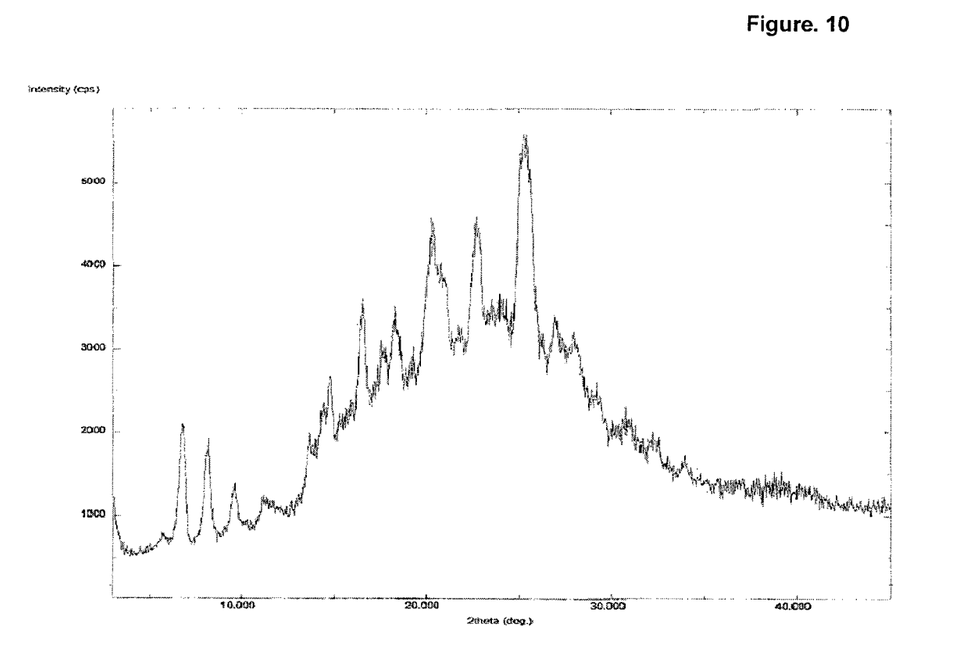
FIG. 10 is the characteristic powder X-ray diffraction (XRD) pattern of Sitagliptin ferulate Form III.

In another embodiment, the present invention provides crystalline sitagliptin ferulate (Form III), characterized by an X-Ray diffraction (XRD) pattern substantially in accordance with FIG. 10.

In another embodiment, the present invention provides crystalline sitagliptin ferulate Isopropyl ether solvate.

Figure 11:
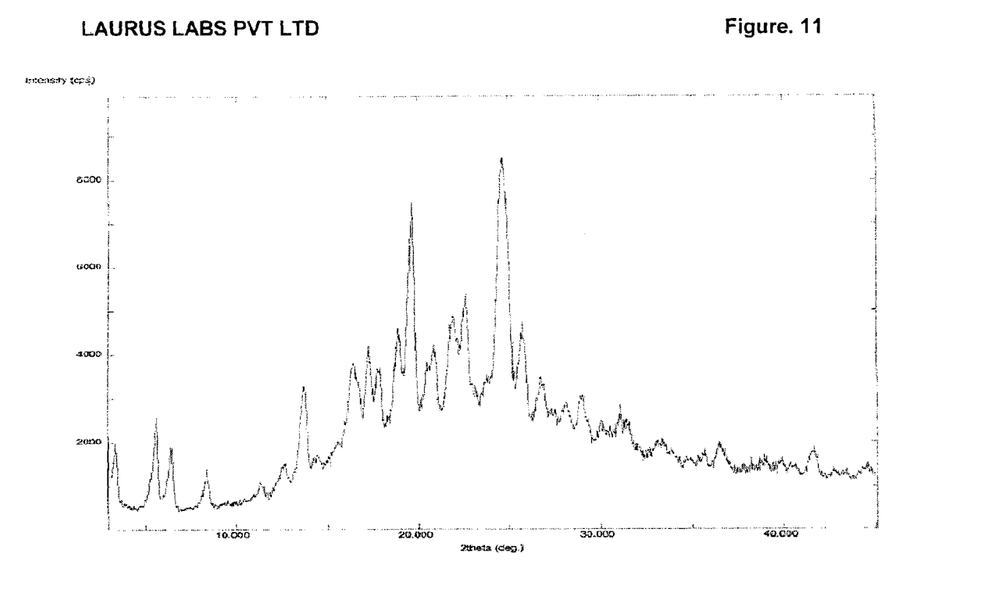
FIG. 11 is the characteristic powder X-ray diffraction (XRD) pattern of Sitagliptin ferulate Form IV.

In another embodiment, the present invention provides crystalline sitagliptin ferulate Isopropyl ether solvate (Form IV), characterized by an X-Ray diffraction (XRD) pattern substantially in accordance with FIG. 11.

Figure 12:
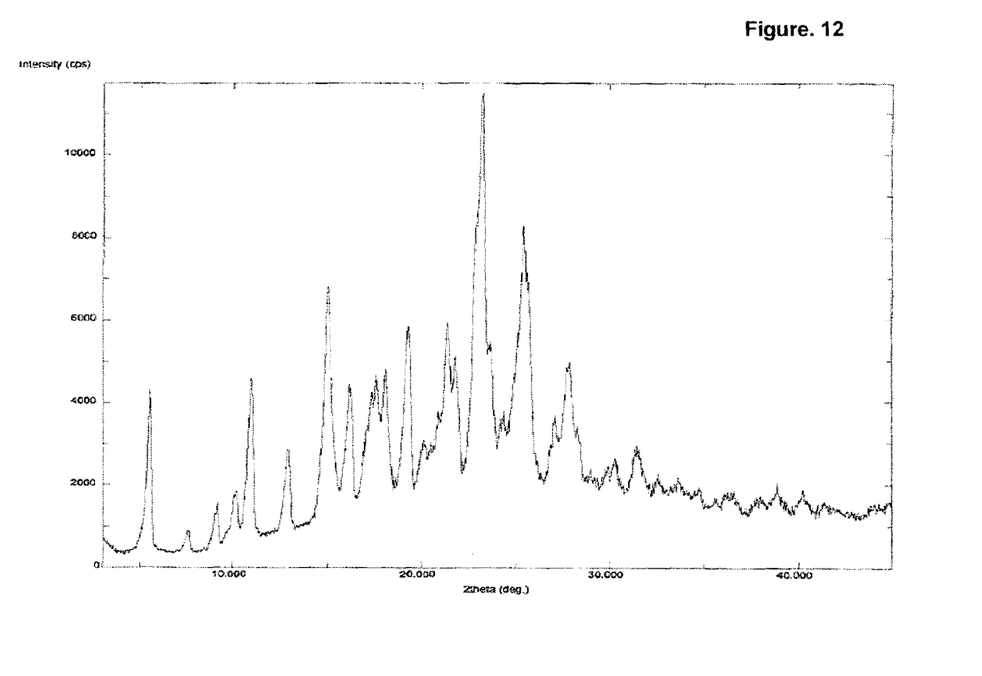
FIG. 12 is the characteristic powder X-ray diffraction (XRD) pattern of Sitagliptin ferulate Form V.

In another embodiment, the present invention provides crystalline sitagliptin ferulate (Form V), characterized by an X-Ray diffraction (XRD) pattern substantially in accordance with FIG. 12.

In another embodiment, the present invention provides sitagliptin ferulate in an amorphous form.

Figure 13:
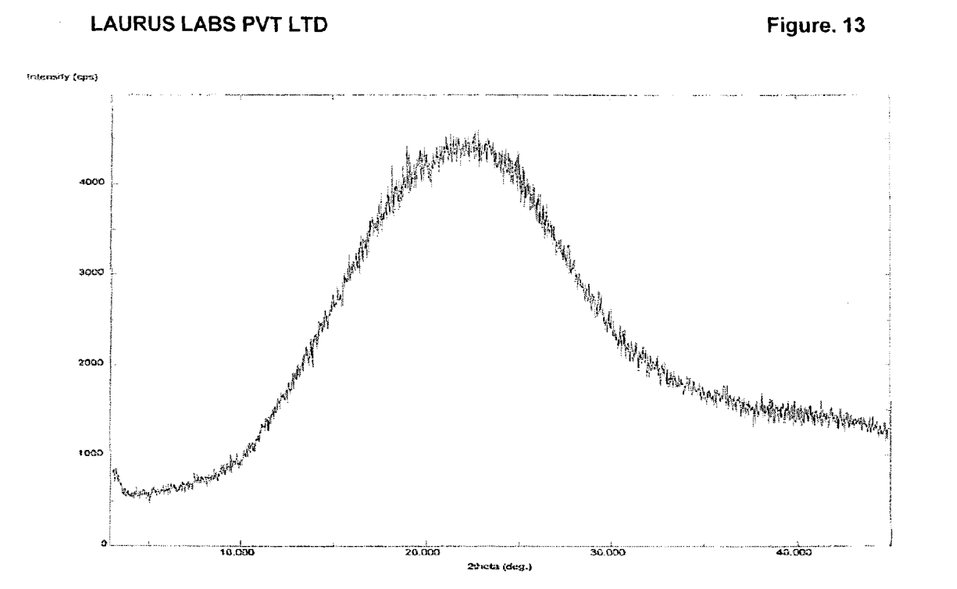
FIG. 13 is the characteristic powder X-ray diffraction (XRD) pattern of Sitagliptin ferulate amorphous Form.

In another embodiment, the present invention provides sitagliptin ferulate in an amorphous form, characterized by an X-Ray diffraction (XRD) pattern substantially in accordance with FIG. 13.

In another embodiment, the present invention provides sitagliptin coumarate or hydrate or solvate thereof.

In another embodiment, the present invention provides sitagliptin coumarate in crystalline form.

In another embodiment, the present invention provides crystalline sitagliptin coumarate Acetonitrile solvate.

Figure 14:
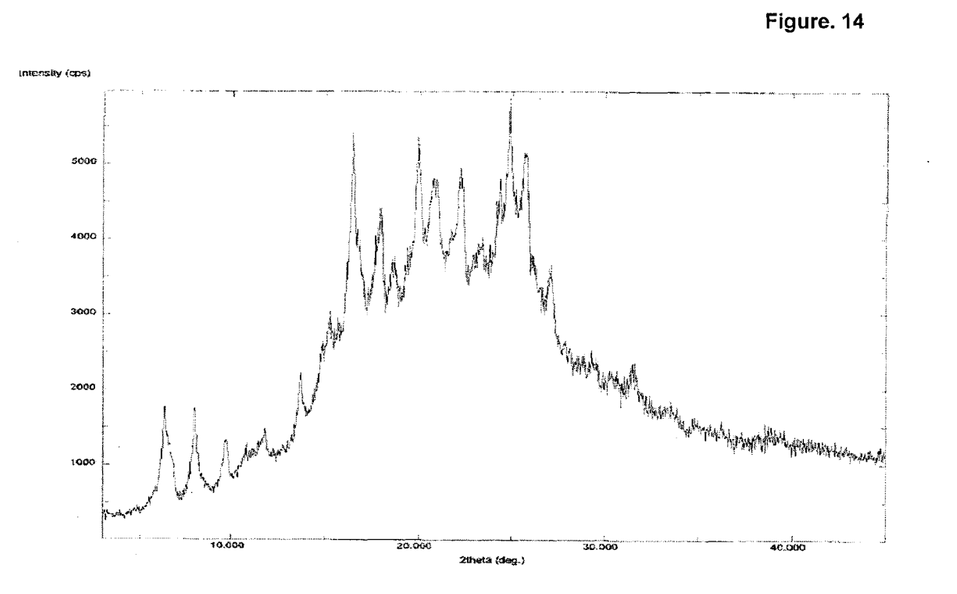
FIG. 14 is the characteristic powder X-ray diffraction (XRD) pattern of Sitagliptin coumarate Form I.

In another embodiment, the present invention provides crystalline sitagliptin coumarate Acetonitrile solvate (Form I), characterized by an X-Ray diffraction (XRD) pattern substantially in accordance with FIG. 14.

Figure 15:
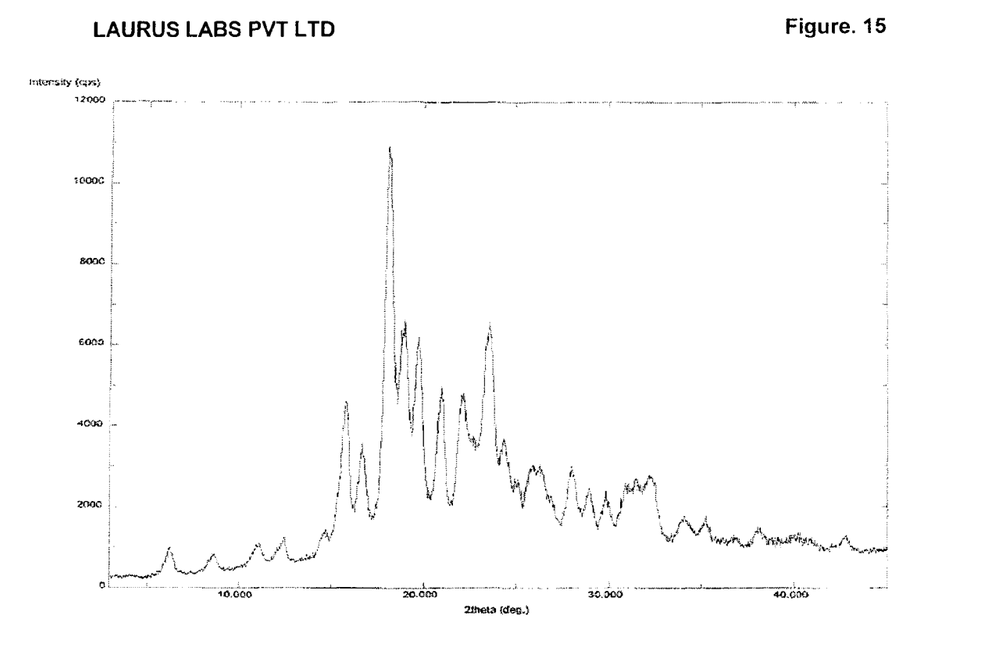
FIG. 15 is the characteristic powder X-ray diffraction (XRD) pattern of Sitagliptin coumarate Form II.

In another embodiment, the present invention provides crystalline sitagliptin coumarate (Form II), characterized by an X-Ray diffraction (XRD) pattern substantially in accordance with FIG. 15.

In another embodiment, the present invention provides crystalline sitagliptin coumarate THF solvate.

Figure 16:
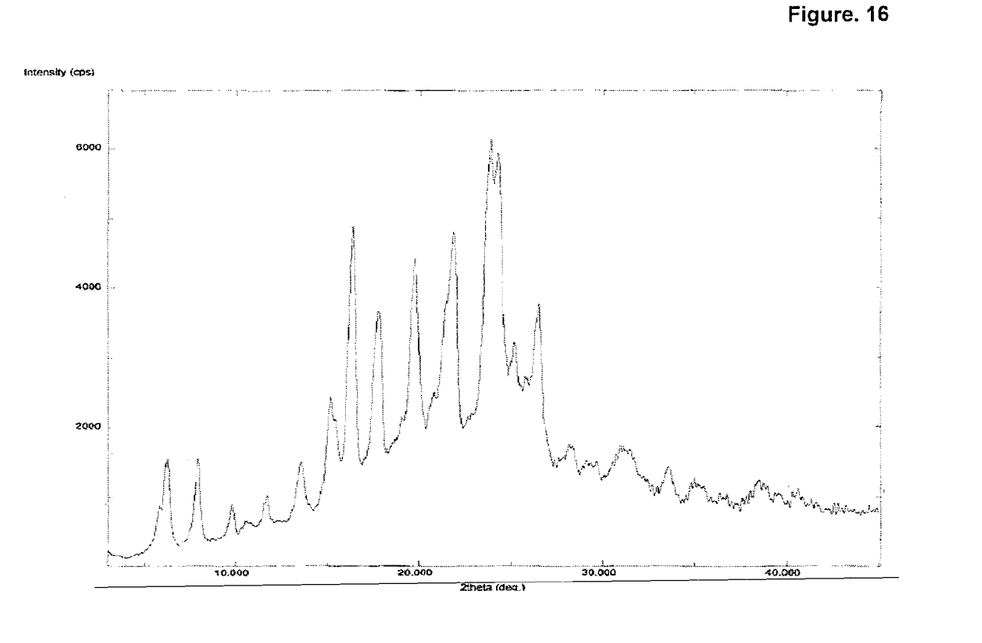
FIG. 16 is the characteristic powder X-ray diffraction (XRD) pattern of Sitagliptin coumarate Form III.

In another embodiment, the present invention provides crystalline sitagliptin coumarate THF solvate (Form III), characterized by an X-Ray diffraction (XRD) pattern substantially in accordance with FIG. 16.

In another embodiment, the present invention provides crystalline sitagliptin coumarate Isopropanol solvate.

Figure 17:
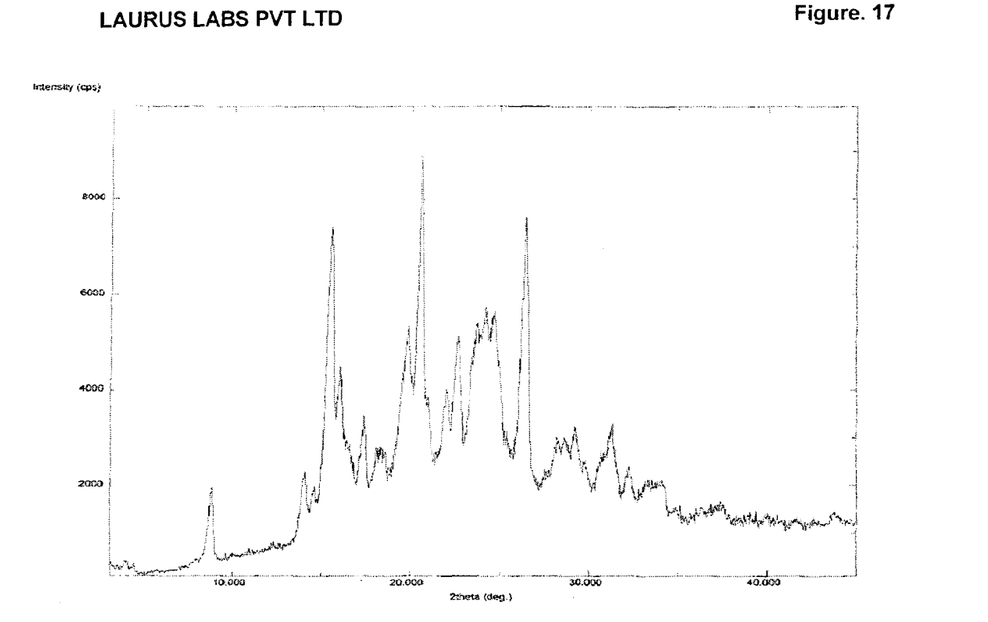
FIG. 17 is the characteristic powder X-ray diffraction (XRD) pattern of Sitagliptin coumarate Form IV.

In another embodiment, the present invention provides crystalline sitagliptin coumarate Isopropanol solvate (Form IV), characterized by an X-Ray diffraction (XRD) pattern substantially in accordance with FIG. 17.

In another embodiment, the present invention provides crystalline sitagliptin coumarate Ethanol solvate.

Figure 18:
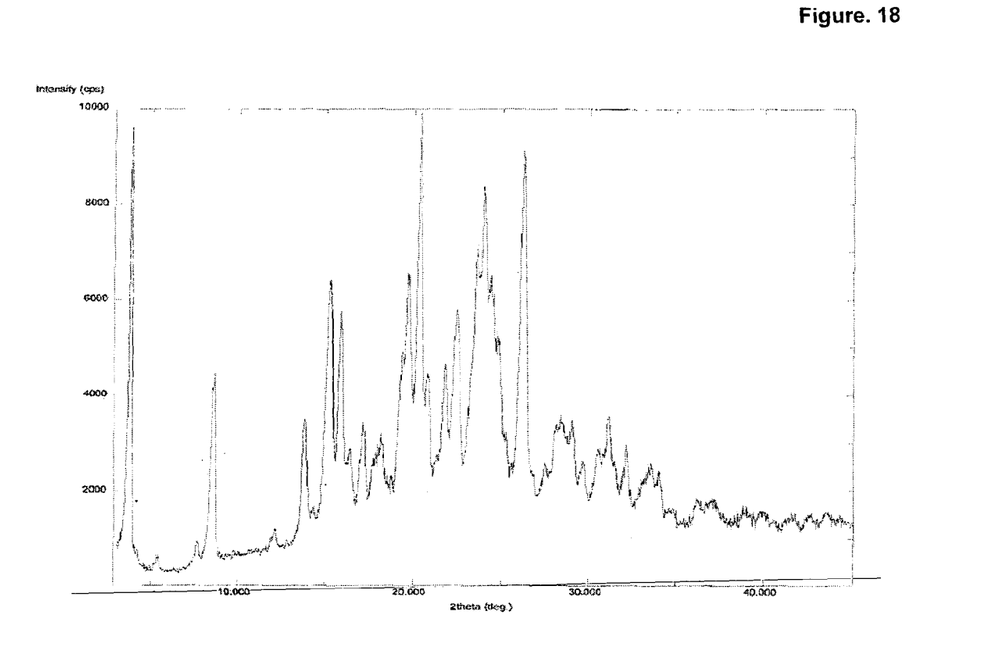
FIG. 18 is the characteristic powder X-ray diffraction (XRD) pattern of Sitagliptin coumarate Form V.

In another embodiment, the present invention provides crystalline sitagliptin coumarate Ethanol solvate (Form V), characterized by an X-Ray diffraction (XRD) pattern substantially in accordance with FIG. 18.

Figure 19:
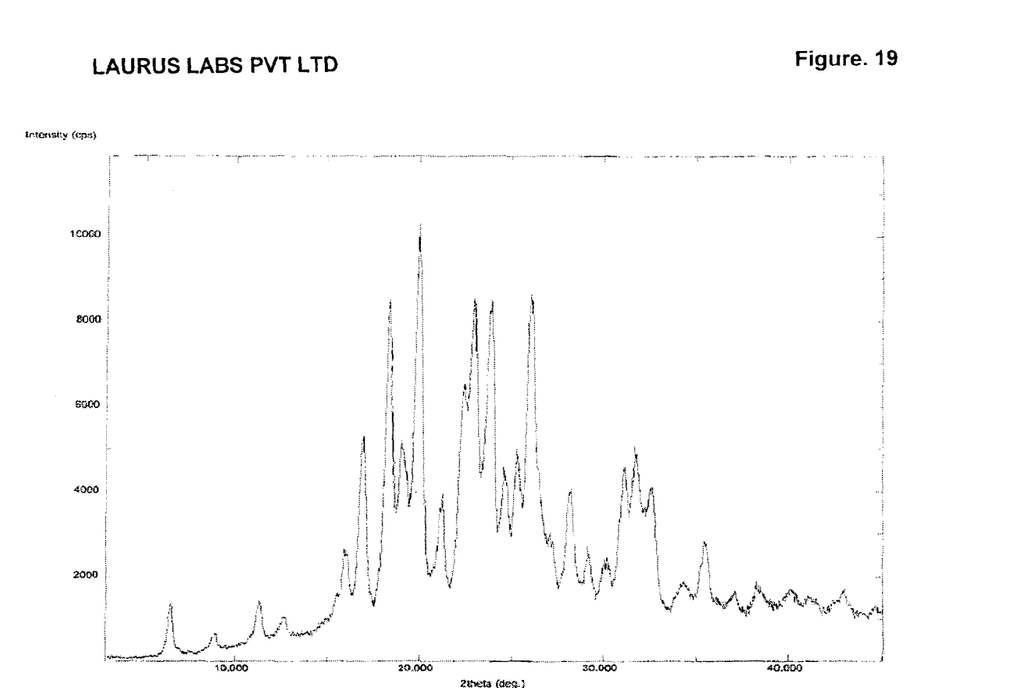
FIG. 19 is the characteristic powder X-ray diffraction (XRD) pattern of Sitagliptin coumarate Form VI.

In another embodiment, the present invention provides crystalline sitagliptin coumarate (Form VI), characterized by an X-Ray diffraction (XRD) pattern substantially in accordance with FIG. 19.

In another embodiment, the present invention provides sitagliptin coumarate in an amorphous form.

Figure 20:
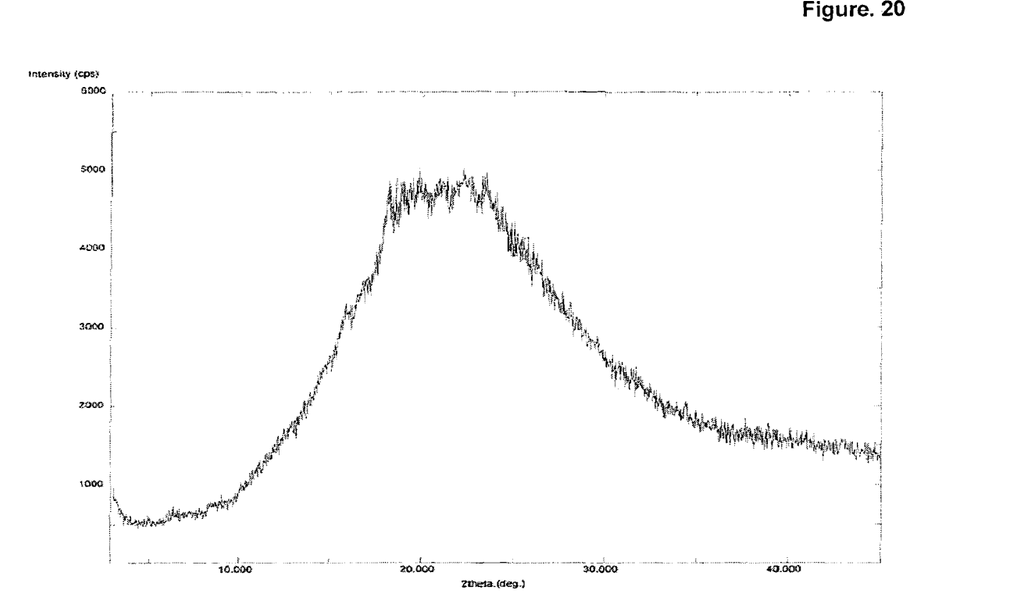
FIG. 20 is the characteristic powder X-ray diffraction (XRD) pattern of Sitagliptin coumarate amorphous Form.

In another embodiment, the present invention provides sitagliptin coumarate in an amorphous form, characterized by an X-Ray diffraction (XRD) pattern substantially in accordance with FIG. 20.

In another embodiment, the present invention provides a process for preparing acid addition salts of sitagliptin comprising a) providing a mixture comprising sitagliptin base and an anti-oxidant acid and b) isolating the acid addition salts of sitagliptin.

In another embodiment of the present invention sitagliptin cinnamate, sitagliptin coumarate, sitagliptin ferulate, sitagliptin sinapate, sitagliptin caffate, sitagliptin chlorogenate, sitagliptin benzoate, sitagliptin p-hydroxy benzoate, sitagliptin vanillate, sitagliptin syringate, sitagliptin protocatechuicate, sitagliptin 4-(4-phenoxybenzoyl)benzoate or sitagliptin quinate is prepared by mixing cinnamic acid, p-coumaric acid, ferulic acid, sinapic acid, caffeic acid, chlorogenic acid, benzoic acid, p-hydroxy benzoic acid, vanillic acid, syringic acid, protocatechuic acid, 4-(4-phenoxybenzoyl)benzoic acid or quinic acid in solid state or in solution to the solution of sitagliptin free base in a solvent; and isolating the acid addition salts of sitagliptin.

The Sitagliptin free base, used in the present invention, can be prepared by any known method for example sitagliptin free base may be synthesized as disclosed in U.S. Pat. No. 6,699,871.

The step of forming a solution of sitagliptin free base may include dissolving any form of sitagliptin free base (including hydrates, solvates etc), in a suitable solvent. Suitable solvents include, but are not limited to water, lower alcohols, ketones, esters, ethers, $C_{5-7}$ linear, branched or cyclic, saturated or unsaturated hydrocarbons, nitriles, halogenated hydrocarbons, or mixtures thereof.

Preferably, the suitable solvents includes, but are not limited to methanol, ethanol, isopropanol, acetone, methyl ethyl ketone, methyl isobutyl ketone, methyl acetate, ethyl acetate, isopropyl acetate, tetrahydrofuran (THF), isopropyl ether (IPE), ter. butyl methyl ether, acetonitrile, propionitrile, methylene chloride, chloroform, toluene, cyclohexane, hexane, heptane and the like and mixtures thereof.

Any conditions which forming the acid addition salts of sitagliptin from solution may be used whereby acid addition salts of sitagliptin formed, for example concentrated by subjecting the solution to heating, cooling the solution to precipitation, crystallization, solvent precipitation, spray drying, freeze drying, agitated thin film evaporator (ATFE) and the like.

In an alternative embodiment, the sitagliptin free base mixed with the anti-oxidant acid compound in a solid phase. Any suitable means for mixing may be used in this step, including commercially-available solid mixers.

This may involve grinding or milling the two solids together or melting one or both components and allowing them to recrystallize. The use of a granulating liquid may improve or may impede solid formation. Non-limiting examples of tools useful for the formation of acid addition salts of sitagliptin may include, for example, an extruder or a mortar and pestle. Further, contacting the sitagliptin free base with the anti-oxidant acid compound may also involve either solubilizing the sitagliptin free base and adding the anti-oxidant acid compound, or solubilizing the anti-oxidant acid compound and adding the sitagliptin free base. Crystallization conditions are applied to the sitagliptin free base and anti-oxidant acid compound. This may entail altering a property of the solution, such as pH or temperature and may require concentration of the solute, usually by removal of the solvent, typically by drying the solution. Solvent removal results in the concentration of both sitagliptin free base and anti-oxidant acid compound increasing over time so as to facilitate crystallization. For example, evaporation, cooling, co-sublimation, or the addition of an antisolvent may be used to crystallize solid forms. In another embodiment, a slurry comprising a sitagliptin free base and an anti-oxidant acid compound is used to form solid forms.

In a preferred embodiment, the present invention provides a process for preparing acid addition salts of sitagliptin, wherein the acid addition salt is caffeic acid, comprising a) providing a solution comprising sitagliptin base and caffeic acid in a suitable solvent and b) isolating the sitagliptin caffeic acid salt.

The suitable solvent for forming sitagliptin caffeic acid salt is selected from any suitable solvent described just as above; preferably the suitable solvent is selected from the group consisting of methanol, ethanol, acetone, THF, acetonitrile, ethyl acetate, IPE and mixtures thereof.

The solution may be formed by heating the mixture at a temperature of about 30° C. to about reflux temperature, preferably about 45° C. to about 75° C. The sitagliptin caffeic acid salt can be isolated by any known techniques such as cooling the solution to precipitation, crystallization, solvent precipitation, spray drying, freeze drying, agitated thin film evaporator (ATFE) and the like.

In another preferred embodiment, the present invention provides a process for preparing acid addition salts of sitagliptin, wherein the acid addition salt is ferulic acid, comprising a) providing a solution comprising sitagliptin base and ferulic acid in a suitable solvent and b) isolating the sitagliptin ferulic acid salt.

The suitable solvent for forming sitagliptin ferulic acid salt is selected from any suitable solvent described just as above; preferably the suitable solvent is selected from the group consisting of acetonitrile, methanol, ethanol, ethyl acetate, IPE and mixtures thereof.

The solution may be formed by heating the mixture at a temperature of about 35° C. to about reflux temperature, preferably about 45° C. to about 75° C. The sitagliptin ferulic acid salt can be isolated by any known techniques such as cooling the solution to precipitation, crystallization, solvent precipitation, spray drying, freeze drying, agitated thin film evaporator (ATFE) and the like.

In another preferred embodiment, the present invention provides a process for preparing acid addition salts of sitagliptin, wherein the acid addition salt is coumaric acid, comprising a) providing a solution comprising sitagliptin base and coumaric acid in a suitable solvent and b) isolating the sitagliptin coumaric acid salt.

The suitable solvent for forming sitagliptin coumaric acid is selected from any suitable solvent described just as above; preferably the suitable solvent is selected from the group consisting of acetonitrile, methanol, ethanol, isopropanol, ethyl acetate, THF, IPE and mixtures thereof.

The solution may be formed by heating the mixture at a temperature of about 35° C. to about reflux temperature, preferably about 45° C. to about 75° C. The sitagliptin coumaric acid salt can be isolated by any known techniques such as cooling the solution to precipitation, crystallization, solvent precipitation, spray drying, freeze drying, agitated thin film evaporator (ATFE) and the like.

The present invention provides characterization of acid addition salt forms of sitagliptin of the present invention characterized by X-ray powder diffraction (XRD) pattern and/or melting point. The X-Ray powder diffraction can be measured by an X-ray powder diffractometer equipped with a Cu-anode ($[\lambda]=1.54$ Angstrom), X-ray source operated at 30 kV, 15 mA and a Ni filter is used to strip K-beta radiation. Two-theta calibration is performed using an NIST SRM 640c Si standard. The sample was analyzed using the following instrument parameters: measuring range=3-45°2θ; step width=0.020°; and scan speed=5°/minute.

In another embodiment, the present invention provides a pharmaceutical composition comprising a therapeutically effective amount of acid addition salt forms of sitagliptin; in particular anti-oxidant acid addition salts of sitagliptin with at least one pharmaceutically acceptable carrier or other excipients. The pharmaceutical composition can be useful for the treatment of type 2 diabetes mellitus. The present invention also provides acid addition salt forms of sitagliptin as described above for use as a medicament, preferably for the treatment of type 2 diabetes mellitus.

The present invention further provides, when a pharmaceutical composition comprising acid addition salt forms of sitagliptin prepared according to the present invention is formulated for oral administration or parenteral administration. Accordingly, D50 and D90 particle size of the unformulated acid addition salt forms of sitagliptin of the present invention used as starting material in preparing a pharmaceutical composition generally is less than 500 microns preferably less than about 300 microns, more preferably less than 200 microns.

Any milling, grinding, micronizing or other particle size reduction method known in the art can be used to bring the acid addition salt forms of sitagliptin of the present invention into any desired particle size range as set forth above.

Acid addition salt forms of sitagliptin in accordance with present invention can be embodied for example in form of tablet, capsules, pellets, granules and suppositories or their combined forms. Pharmaceutical composition in accordance with present invention can be suitable for immediate release or modified release of sitagliptin salts of the present invention. Solid pharmaceutical compositions can be for example coated with aim of increasing pelletibility or regulating the disintegration or absorption.

Unless defined otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described.

Unless stated to the contrary, any use of the words such as "including," "containing," "comprising" and the like, means "including without limitation" and shall not be construed to limit any general statement that it follows to the specific or similar items or matters immediately following it. Embodiments of the invention are not mutually exclusive, but may be implemented in various combinations.

For purposes of the present invention, the following terms are defined below.

The term "composition" includes, but is not limited to, a powder, a suspension, an emulsion and/or mixtures thereof. The term composition is intended to encompass a product containing the specified ingredients in the specified amounts, as well as any product, which results, directly or indirectly, from combination of the specified ingredients in the specified amounts. A "composition" may contain a single compound or a mixture of compounds.

The term "co-crystal" as used herein means a crystalline material comprised of two or more unique solids at room temperature, each containing distinctive physical characteristics, such as structure, melting point and heats of fusion.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Example 1

Preparation of Sitagliptin Caffate Form I

Charged 4 gms of caffeic acid and 40 ml of ethanol in a round bottom flask at temperature 25° C. to 35° C. Stirred for 4 hours at same temperature and sitagliptin free base (4.86 gms) was added to the resultant clear solution. Stirred for 48 hours at same temperature and the precipitated solids were filtered off and dried at 70° C. to 75° C. for 12 hours to obtain the title compound. Yield: 3.86 gms.

The XRPD is set forth in FIG. 1.

1H NMR (DMSO d6): δ 1.027 (3H, t, J=7.02 Hz), 3.41 (2H, q, J=7.01 Hz)

DSC: 130.63° C., 144.38° C., 178.56° C.

Example 2

Preparation of Sitagliptin Caffate Form II

Sitagliptin free base (2.0 gms) and caffeic acid (0.88 gms) were dissolved in methanol (20 ml) at 60° C. to 65° C. and the solution was cooled to room temperature. Slowly isopropyl ether (120 ml) was added to the resultant clear solution and stirred for 14 hours at same temperature. Precipitated solids were filtered off and dried at 50° C. to 55° C. for 6 hours to obtain the title compound. Yield: 1.65 gms.

The XRPD is set forth in FIG. 2.

1H NMR (DMSO d6): δ1.01 (12H, d, J=6.06 Hz), 3.57 (2H, J=6.02 Hz)

DSC: 126.13° C., 141.12° C., 166.41° C.

Example 3

Preparation of Sitagliptin Caffate Form III

Sitagliptin free base (2.0 gms) and caffeic acid (0.88 gms) were dissolved in acetone (80 ml) at 60° C. to 65° C. and the reaction mass left for slow solvent evaporation at room temperature for 24 hours. Precipitated solids were filtered off and dried at 70° C. to 75° C. for 12 hours to obtain the title compound.

Yield: 1.53 gms

The XRPD is set forth in FIG. 3.

1H NMR (DMSO d6): δ 2.09 (6H, s)

DSC: 150.11° C., 181.59° C.

Example 4

Preparation of Sitagliptin Caffate Form IV

Sitagliptin free base (2.0 gms) and caffeic acid (0.88 gms) were dissolved in Tetrahydrofuran (120 ml) at 60° C. to 65° C. and the reaction mass left for slow solvent evaporation at room temperature for 10 hours. Precipitated solids were filtered off and dried at 70° C. to 75° C. for 12 hours to obtain the title compound.

Yield: 1.45 gms

The XRPD is set forth in FIG. 4

1H NMR (DMSO d6): δ 1.73 (4H, m), 3.56 (4H, m)

Example 5

Preparation of Sitagliptin Caffate Form V

Sitagliptin free base (2.0 gms) and caffeic acid (0.88 gms) were dissolved in acetonitrile (160 ml) at 60° C. to 65° C. and the reaction mass left for slow solvent evaporation at room temperature for 24 hours. Precipitated solids were filtered off and dried at 70° C. to 75° C. for 12 hours to obtain the title compound.

Yield: 1.58 gms

The XRPD is set forth in FIG. 5.

1H NMR (DMSO d6): δ 2.05 (3H, s)

DSC: 110.37° C., 132.35° C., 143.74° C.

Example 6

Preparation of Sitagliptin Caffate Form VI

Sitagliptin free base (2.0 gms) and caffeic acid (0.88 gms) were dissolved in ethyl acetate (200 ml) at 60° C. to 65° C. and the reaction mass left for slow solvent evaporation at room temperature for 24 hours. Precipitated solids were filtered off and dried at 70° C. to 75° C. for 12 hours to obtain the title compound.

Yield: 1.62 gms

The XRPD is set forth in FIG. 6.

1H NMR (DMSO d6): δ 1.15 (3H, t, J=7.1 Hz), 1.96 (3H, s), 4.04 (2H, q)

DSC: 138.46° C., 154.95° C., 185.57° C.

Example 7

Preparation of Sitagliptin Caffate Amorphous Form

Sitagliptin free base (0.5 gms) and caffeic acid (0.22 gms) were dissolved in methanol (5.0 ml) at 60° C. to 65° C. and the solution was cooled to room temperature. Slowly isopropyl ether (30 ml) was added to the resultant clear solution and stirred for 2 hours. Precipitated solids were filtered off and dried at 50° C. to 55° C. for 12 hours to obtain the title compound.

Yield: 0.42 gms.

The XRPD is set forth in FIG. 7.

Example 8

Preparation of Sitagliptin Ferulate Form I

Sitagliptin free base (2.0 gms) and ferulic acid (0.95 gms) were dissolved in acetonitrile (16 ml) at 60° C. to 65° C. and the reaction mass left for slow solvent evaporation at room temperature for 48 hours. Precipitated solids were filtered off and dried at 50° C. to 55° C. for 6 hours to obtain the title compound. Yield: 1.45 gms.

The XRPD is set forth in FIG. 8.

1H NMR (DMSO d6): δ 2.05 (3H, s)

DSC: 110.35° C., 151.29° C.

Weight loss by TGA: 3.310%

Example 9

Preparation of Sitagliptin Ferulate Form II

Sitagliptin free base (4.0 gms) and ferulic acid (1.90 gms) were dissolved in ethyl acetate (32 ml) at 60° C. to 65° C. and the resultant clear solution left for slow solvent evaporation at room temperature for 48 hours. Precipitated solids were filtered off and dried at 50° C. to 55° C. for 6 hours to obtain the title compound. Yield: 3.48 gms.

The XRPD is set forth in FIG. 9.

DSC: 99.39° C., 163.58° C.

Weight loss by TGA: 0.964%

Example 10

Preparation of Sitagliptin Ferulate Form III

Ferulic acid (2.0 gms) was dissolved in ethanol (10 ml) and sitagliptin free base (1.9 gms) was added to the clear solution and stirred for 15 min. Additional ethanol (10 ml) was added to the semi precipitated reaction mass and stirring was continued for 48 hours at room temperature. Precipitated solids were filtered off and dried at 70° C. to 75° C. for 24 hours to obtain the title compound. Yield: 1.37 gms.

The XRPD is set forth in FIG. 10.
DSC: 76.02° C., 159.33° C.
Weight loss by TGA: 2.763%

Example 11

Preparation of Sitagliptin Ferulate Form IV

Sitagliptin free base (2.0 gms) and ferulic acid (0.95 gms) were dissolved in methanol (12 ml) at 60° C. to 65° C. and the resultant solution was cooled to room temperature. Isopropyl ether (120 ml) was added to the clear solution and stirred for 12 hours. Filtered the precipitated solids and dried at 70° C. to 75° C. for 12 hours to obtain the title compound.

Yield: 1.21 gms.
The XRPD is set forth in FIG. 11.
1H NMR (DMSO d6): δ 1.01 (12H, d, J=6.03 Hz), 3.57 (2H, m, J=6.02 Hz)
DSC: 158.56° C.
Weight loss by TGA: 2.15%.

Example 12

Preparation of Sitagliptin Ferulate Form V

Sitagliptin free base (0.25 gms) and ferulic acid (0.12 gms) were dissolved in ethyl acetate (2 ml) at 60° C. and the resultant solution was left for slow solvent evaporation at room temperature for 30 hours. Precipitated solids were filtered off and suck dried to obtain the title compound. Yield: 0.31 gms.

DSC: 93.47° C., 188.42° C.

Example 13

Preparation of Sitagliptin Ferulate Amorphous Form

Sitagliptin free base (0.5 gms) and ferulic acid (0.25 gms) were dissolved in methanol (3 ml) at 60° C. to 65° C. and the solution was cooled to room temperature. Isopropyl ether (25 ml) was added to the clear solution and stirred for 2 hours. Filtered the precipitated solids and allowed for suck dry for 30 minutes to obtain the title compound. Yield: 0.42 gms.

The XRPD is set forth in FIG. 12.

Example 14

Preparation of Sitagliptin Coumarate Form I

Sitagliptin free base (2.0 gms) and coumaric acid (0.80 gms) were dissolved in acetonitrile (15 ml) at 60° C. to 65° C. and cooled the solution to −10° C. to −5° C. over a period of 6 hours. Precipitated solids were filtered and dried at 50° C. to 55° C. for 6 hours to obtain the title compound. Yield: 1.62 gms.

The XRPD is set forth in FIG. 13.
1H NMR (DMSO d6): δ 2.05 (3H, s)
DSC: 104.05° C., 170.98° C.
Weight loss by TGA: 2.427%.

Example 15

Preparation of Sitagliptin Coumarate Form II

Sitagliptin free base (2.0 gms) and coumaric acid (0.80 gms) were dissolved in methanol (12 ml) at 60° C. to 65° C. and the solution was cooled to room temperature. Isopropyl ether (240 ml) was added to the resultant clear solution and stirred for 14 hours. Precipitated solids were filtered and dried at 50° C. to 55° C. for 6 hours to obtain the title compound.

Yield: 2.05 gms.
The XRPD is set forth in FIG. 14.
1H NMR (DMSO d6): δ 1.01 (12H, d, J=6.03 Hz) 3.57 (2H, m, J=6.02 Hz)
DSC: 170.35° C.
Weight loss by TGA: 0.3096%.

Example 16

Preparation of Sitagliptin Coumarate Form III

Sitagliptin free base (2.0 gms) and coumaric acid (0.80 gms) were dissolved in Tetrahydrofuran (100 ml) at 60° C. to 65° C. and the resultant solution left for slow solvent evaporation at room temperature for 18 hours. Precipitated solids were filtered and dried at 50° C. to 55° C. for 6 hours to obtain the title compound.

Yield: 2.12 gms
The XRPD is set forth in FIG. 15.
1H NMR (DMSO d6): δ 1.73 (4H, m), 3.56 (4H, m)
DSC: 141.71° C., 180.16° C.
Weight loss by TGA: 4.783%.

Example 17

Preparation of Sitagliptin Coumarate Form IV

Sitagliptin free base (0.25 gms) and coumaric acid (0.10 gms) were dissolved in Isopropanol (4 ml) at 60° C. to 65° C. and the resultant solution left for slow solvent evaporation at room temperature for 48 hours. Precipitated solids were filtered and dried at 50° C. to 55° C. for 4 hours to obtain the title compound. Yield: 0.14 gms.

The XRPD is set forth in FIG. 16.
1H NMR (DMSO d6): δ 1.01 (6H, d, J=6.09 Hz), 3.57 (1H, m, J=6.02 Hz)
DSC: 143.50° C., 158.76° C.
Weight loss by TGA: 0.35%.

Example 18

Preparation of Sitagliptin Coumarate Form V

Sitagliptin free base (0.25 gms) and coumaric acid (0.10 gms) were dissolved in ethanol (2 ml) at 60° C. to 65° C. and the resultant solution left for slow solvent evaporation at room temperature for 48 hours. Precipitated solids were filtered and dried at 50° C. to 55° C. for 4 hours to obtain the title compound. Yield: 0.12 gms.

The XRPD is set forth in FIG. 17.
1H NMR (DMSO d6): δ 1.03 (3H, t, J=7.02 Hz), 3.41 (2H, q, J=7.01 Hz)
DSC: 146.46° C., 176.51° C., 204.57° C.
Weight loss by TGA: 0.55%.

Example 19

Preparation of Sitagliptin Coumarate Form VI

Sitagliptin free base (2.0 gms) and coumaric acid (0.80 gms) were dissolved in ethyl acetate (32 ml) at 60° C. to 65° C. and the resultant reaction solution left for slow solvent evaporation at room temperature for 2 hours. Precipitated solids were filtered and dried at 50° C. to 55° C. for 6 hours to obtain the title compound.

Yield: 2.01 gms
The XRPD is set forth in FIG. 18.
DSC: 170.78° C., 200.34° C.
Weight loss by TGA: 0.68%.

Example 20

Preparation of Sitagliptin Coumarate Amorphous Form

Sitagliptin free base (0.5 gms) and coumaric acid (0.20 gms) were dissolved in methanol (3 ml) at 60° C. to 65° C. and the resultant solution was cooled to room temperature. Isopropyl ether (60 ml) was added to the resultant clear solution and stirred for 2 hours. Precipitated solids were filtered and suck dried for 20 minutes to obtain the title compound. Yield: 0.38 gms.

The XRPD is set forth in FIG. 19.
1H NMR (DMSO d6): δ 1.01 (12H, d, J=6.03 Hz), 3.57 (2H, =6.02 Hz)
Weight loss by TGA: 6.67%.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. An anti-oxidant acid salt of sitagliptin, or solvates or hydrates thereof, wherein the anti-oxidant acid is selected from the group consisting of caffeic acid, ferulic acid, and p-coumaric acid, and wherein
    the caffeic acid salt of sitagliptin is characterized by a X-ray diffraction (XRD) pattern in accordance with FIG. 1, FIG. 2, FIG. 3, FIG. 4, FIG. 5, FIG. 6, or FIG. 7,
    the ferulic acid salt of sitagliptin is characterized by a XRD pattern in accordance with FIG. 8, FIG. 9, FIG. 10, FIG. 11, FIG. 12, or FIG. 13, and
    the p-coumaric acid salt of sitagliptin is characterized by a XRD pattern in accordance with FIG. 14, FIG. 15, FIG. 16, FIG. 17, FIG. 18, FIG. 19, or FIG. 20.

2. A composition comprising sitagliptin caffeate, sitagliptin ferulate, sitagliptin coumarate, or solvates or hydrates thereof, and at least one pharmaceutically acceptable carrier or excipient, wherein
    the sitagliptin caffeate is characterized by a X-ray diffraction (XRD) pattern in accordance with FIG. 1, FIG. 2, FIG. 3, FIG. 4, FIG. 5, FIG. 6, or FIG. 7,
    the sitagliptin ferulate is characterized by a XRD pattern in accordance with FIG. 8, FIG. 9, FIG. 10, FIG. 11, FIG. 12, or FIG. 13, and
    the sitagliptin coumarate is characterized by a XRD pattern in accordance with FIG. 14, FIG. 15, FIG. 16, FIG. 17, FIG. 18, FIG. 19, or FIG. 20.

* * * * *